United States Patent [19]

O'Connell

[11] 4,097,943
[45] Jul. 4, 1978

[54] ABSORBENT PAD

[75] Inventor: Thomas Christopher O'Connell, Dartray, Ireland

[73] Assignee: Johnson & Johnson, New Brunswick, N.J.

[21] Appl. No.: 747,135

[22] Filed: Dec. 3, 1976

[30] Foreign Application Priority Data

Dec. 9, 1975 [GB] United Kingdom ............... 50427/75

[51] Int. Cl.² ........................................... A61F 13/16
[52] U.S. Cl. ............................................. 5/335; 5/92;
5/334 R; 128/275
[58] Field of Search ............................ 5/92, 334, 335;
128/275, 287, 288, 291, 292, 296

[56] References Cited

U.S. PATENT DOCUMENTS

| 3,113,326 | 12/1963 | Hyde et al. | 5/335 |
| 3,315,677 | 4/1967 | Tyrrell, Jr. | 128/288 |
| 3,643,662 | 2/1972 | McGuire et al. | 128/288 |
| 3,871,037 | 3/1975 | Willington | 5/92 |
| 3,888,255 | 6/1975 | Shah et al. | 128/288 |
| 3,987,792 | 10/1976 | Hernandez | 128/287 |
| 4,000,028 | 12/1976 | Hoey | 128/296 |

Primary Examiner—Casmir A. Nunberg

[57] ABSTRACT

An absorbent pad which comprises a fluid-impervious backing sheet, a fluid-absorbent fabric adhering to one face of the backing sheet, and at least two strips of pressure-sensitive adhesive affixed on edge portions of the other face of the backing sheet for adhering the pad to a substrate, preferably in the form of a unitized underpad wherein the absorbent fabric layer is fully adhesively laminated to the impervious backing sheet. Preferably the adhesive strips are provided in the form of tape bearing pressure-sensitive on both sides thereof, one side of such tape being adhered to the exposed surface of the backing sheet, the adhesive strength on one side of the tape being greater than the adhesive strength on the other side of the tape.

10 Claims, 1 Drawing Figure

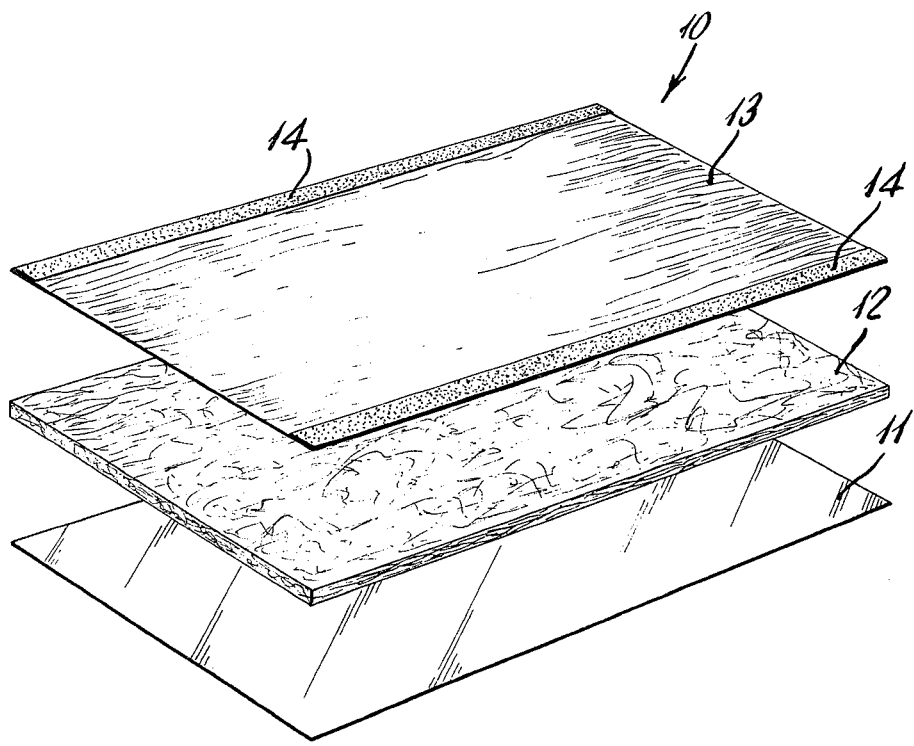

ABSORBENT PAD

The present invention relates to absorbent pads suitable for use over hospital bedding beneath incontinent patients and accordingly referred to herein as incontinence pads although their usefulness is not restricted to this specific purpose. Such pads are required to absorb fluids exuded from the body such as blood, menstrual fluid, urine and the fluid content of faeces.

Apart from the effective performance of their absorbent function, incontinence pads should not create discomfort to the patient by virtue for instance of thickness, shape or texture, and should be capable of being readily put into position, withdrawn or replaced, even when the patient must remain in the bed. Above all they should stay in place when installed and not shift about in the bed. Incontinence pads are preferably disposable and should not be expensive to provide.

Pads, towels or other materials adopted for this purpose hitherto, have generally failed to meet all these criteria. We have found that a particular composite material is highly acceptable as an incontinence pad and fulfils the foregoing and other requirements.

Accordingly the present invention provides an absorbent pad which comprises a fluid-impervious backing sheet, a fluid-absorbent fabric adhering to one face of the backing sheet, and at least two strips of pressure-sensitive adhesive affixed on edge portions of the other face of the backing sheet for adhering the pad to a substrate such as bedding. The pad may be provided with a fluid-pervious facing layer covering the absorbent fabric on the face thereof away from the backing sheet. The instant invention may be more easily understood by reference to the FIGURE.

The FIGURE is an exploded perspective view of an underpad 10 in accordance with the instant invention. 11 Represents the fluid pervious facing layer, 12 represents the fluid absorbent fabric and 13 + represents the fluid impervious backing sheet. Affixed to said fluid impervious backing sheet at the edges thereof are two strips of adhesive, 14.

Any pressure-sensitive adhesive may be used, e.g., an acrylic adhesive such as a polyacrylate or polymethacrylate. Preferably the layer of pressure-sensitive adhesive is provided with a releasable cover sheet. The adhesive may contain medicinal products, e.g., antiseptics.

In general the pad of the invention will be rectangular and have two long edges. One of the pressure-sensitive adhesive strips should be adjacent to one long edge of the backing sheet if not actually at the edge, and the other or another pressure-sensitive adhesive strip should be adjacent to or at another long edge of the backing sheet, thereby facilitating secure positioning of the pad by the effective fastening down of its long edges on the bedding beneath a patient. With the adhesive strips in these positions the pad can be inserted under, or removed from, a patient with minimum disturbance to the latter.

Further adhesive strips may be added in other locations or portions of the backing sheet.

Advantageously the adhesive strips are provided in the form of a double faced pressure-sensitive adhesive tape having one adhesive face adhered to the exposed surface of the backing sheet, for temporarily adhering the pad by means of the second adhesive face, to a substrate such as bedding, the adhesive strength of said one adhesive face of the tape being higher than the adhesive strength of said second adhesive face of the tape.

The adhesive strength is defined as that force required under normal atmospheric conditions to strip or peel away at an angle of at least 90° a double faced, pressure-sensitive adhesive tape which has been firmly secured by one of its adhesive faces to the surface of a flat stainless steel plate and is quantified as ounces per inch of tape width.

Preferably, said second adhesive face is protected by a removable release strip. The release strip is, of course, removed before use of the pad.

Preferably, the adhesive strength of said one adhesive face is from about 30 to about 112 ounces/inch width and the adhesive strength of said second adhesive face is from about 20 to about 49 ounces/inch width and the ratio between the adhesive strengths of said one adhesive face and said second adhesive face is from about 1.5:1 to about 2.5:1.

More preferably, the adhesive strength of said one adhesive face is from about 60 to about 68 ounces/inch width and the adhesive strength of said second adhesive face is from about 32 to about 37 ounces/inch width and the ratio between the adhesive strengths of said one adhesive face and said second adhesive face is from about 1.9:1 to about 2.1:1.

The double faced adhesive tape includes a thin film-like substrate, with an adhesive coating on one surface for securing the substrate to the backing sheet and an adhesive coating on the opposite, i.e., outside, surface of the substrate, for adhering the pad to a fabric such as bedding.

The release strip can be of any suitable film-like material that does not adhere too tenaciously to the adhesive coating, and particularly suitable is a semi-bleached, Kraft paper one side of which has been silicone-coated to provide for easy release of the paper strip from the outer adhesive layer.

The differential adhesive strengths required by the double-faced pressure-sensitive adhesive tape preferably used in the present invention can be obtained in several ways. The adhesive tape can be made by providing a substrate with two chemically different pressure-sensitive adhesives applied to the opposite sides thereof. For example, a first adhesive layer for permanent attachment to the backing sheet can be a high tack, natural crepe rubber, polyisoprene base adhesive while the other or second adhesive layer can be a low tack, acrylic copolymer base adhesive. Each of the adhesives can be formulated to meet the adhesive strength requirements set forth above, by any skilled chemist familiar with the field of pressure-sensitive adhesives.

The thin film-like substrate for the double-faced adhesive tape can, for example, be Mylar, Kraft paper, cellulose acetate or bleached sulphite tissue.

By using the chemically different, pressure-sensitive adhesives on opposite sides of the substrate, the built-in integrity of the rubber based adhesive layer and the built-in integrity of the acrylic copolymer base adhesive layer is maintained without migration of adhesion properties across the substrate, whether made of pervious (bleached sulphite tissue) or impervious (cellulose acetate) material, because of the inherent incompatibility of the different adhesives used. The rubber base adhesive, having the high degree of tack, assures permanent attachment of the tape to the backing sheet while the softer, low tack acrylic adhesive assures excellent adhesion to fabrics such as bedding regardless of the yarns from which the fabrics are made because the bond not only adheres well to the surface of yarns because of its physical nature, but actually flows in and around the interstices of the fabric multiplying the surface area of contact. Because of the integrity of the acrylic copolymer adhesive, however, the tape readily releases cleanly from the fabrics on the application of a positive and directional pull without leaving residues of adhesive.

Differential adhesion can also be imparted to the adhesive tape when chemically similar pressure-sensitive adhesives are used for the adhesive layers. For example, one adhesive layer can be an acrylic copolymer base adhesive formulated so as to have a high adhesive strength and the other adhesive layer can be a similar acrylic copolymer base adhesive but formulated to have a lower adhesive strength, each of the adhesive strengths obtained falling within the ranges set forth hereinabove. However, when chemically similar adhesives are used for the adhesive layers the substrate must be of an impervious material, such as cellulose acetate or Mylar, to prevent migration of adhesion properties from one adhesive layer to the other adhesive layer. If such migration were to occur, the adhesion levels would, after a short period of time, equalize, thus rendering the adhesive tape unsuitable for its intended purpose.

Yet another way for obtaining differential adhesive strengths for the tape is to use either chemically different pressure-sensitive adhesives or chemically similar pressure-sensitive adhesives for the adhesive layers but to reduce the surface area of the adhesive application on the side of the substrate which is to be placed adjacent the fabric material such as bedding. This can be accomplished by forming the latter adhesive layer with an intermittent pattern of adhesive such as, for example, longitudinally extending, transversely spaced adhesive lines: transversely extending longitudinally spaced adhesive lines: adhesive lines coated in a rectangular or diamond pattern: or intermittent spots of adhesive. The intermittent patterns of adhesive can be applied to the substrate by any of the well-known printing techniques.

The preferred pad according to the invention includes an absorbent fabric core covered over the top surface by a fluid-pervious cover and over the bottom surface by a fluid-impervious backing sheet for the purpose of preventing strike-through of absorbed body exudates. The absorbent core layer can be made from woven fabrics, paper, inherently hydrophilic foams, e.g., viscose rayon foam, natural or synthetic foamed polymeric material, e.g., polyurethane, polyether, or styrene/butadiene rubber foams which have been rendered hydrophilic or readily wettable, comminuted wood pulp, cotton linters, and cotton wool of any grade, rayon fibres, cotton staple and bleached or unbleached-creped tissue. The absorbent layer is thus preferably of cellulosic material or of hydrophilic foamed synthetic resin.

Preferably the backing sheet, which constitutes a barrier to liquids, includes or consists of a plastics film, e.g., a polypropylene, polyethylene or polyvinyl chloride film, which may advantageously be embossed, and coloured for ready identification in a hospital context. Polypropylene film may be preferred if it is desired to steam-sterilise the pad; polyethylene is preferred. Other materials may be used to provide the backing, e.g., regenerated cellulose film, impregnated fluid repellent paper, Kraft paper coated with polyethylene or other suitable polymer, water-impervious fabrics such as the material sold by us under the Trade Mark "Barrier", or polymer-coated crepe tissue. Thin metal films may also be employed.

The fluid pervious and preferably non-wettable cover, when present, can be for example a knitted, woven or nonwoven fabric, such as wax-impregnated "Keybak" nonwoven fabric bonded and treated with a water-repellent agent. Alternatively the cover may be of perforated paper or a polymer net. The cover may extend slightly beyond the absorbent fabric and be secured by an adhesive to the backing sheet. The backing sheet may be folded over the fabric at the edges and secured to prevent liquid penetrating out of the pad sideways.

The backing sheet is secured by adhesive to the bottom surface of the absorbent fabric. Preferably the layer of absorbent fabric and the backing sheet are substantially coextensive but the backing may extend beyond an edge or edges of the absorbent layer.

A specific embodiment of the invention will now be described by way of example.

An incontinence pad is made rectangular, e.g., approximately 76 cm × 55 cm and comprises a layer of absorbent material constituted by a central strip of four-ply absorbent unbleached crepe tissue, each ply of crepe tissue weighing approximately 25.5 gm/m$^2$. The layer of absorbent material has on its under-surface a liquid-impervious backing sheet, i.e., a film of 25-micron opaque blue polyethylene. The two long edges of the backing sheet are folded over approximatey an inch to form a barrier to liquids escaping through the edges of the pad.

Two long edge portions of the exposed surface of the backing sheet are each provided along the length of the pad with pressure-sensitive adhesive in the form of two strips of double-sided pressure-sensitive adhesive tape applied to the backing sheet about 5 cm in from each edge, each tape being covered with a silicone impregnated release paper.

The backing sheet and absorbent fabric are held together by means of lines of glue applied at 1-inch intervals across the inner surface of the polyethylene.

A facing layer of water-repellent nonwoven fabric of approximately 70 g/m$^2$ is provided on the face of the absorbent fabric away from the backing sheet.

When placed beneath an incontinent patient in bed, the cover or facing layer allows, and in fact encourages, body fluids to pass into the absorbent fabric which will absorb body fluids, but penetration of the fluids into the bedding is prevented by the backing sheet which acts as a barrier. No additional means are necessary to hold the pad in place. The pad is discarded after a single use, during which it not only protects the bedding but presents to the patient a less uncongenial surface than pads used hitherto, by reason of the efficient action of the pad in conducting fluid away from the facing surface. The pad provides improved, convenient and effective means of dealing favourably with incontinence in bed.

The pad may be produced by extrusion coating a backing layer of polyethylene onto one surface of an absorbent fabric web, applying a strip of double-sided pressure-sensitive adhesive tape to each of the longitudinal edge portions of the backing layer after the original edges of the layer have been folded over the fabric and secured, and applying the releasable cover sheet to the strip for protection. The web may then be cut transversely to desired lengths by guillotine.

Although the pad of the invention has been exemplified above by reference to particular materials and dimensions and other features it will be appreciated that variations may be made, especially as to size, without departing from the spirit and scope of the invention as determined by the appended claims.

What is claimed is:

1. An underpad which comprises a fluid-impervious backing sheet, a fluid absorbent fabric fully adhesively laminated to one face of the backing sheet, a fluid pervious facing layer covering the absorbent fabric on the face thereof away from the backing sheet, and at least two strips of pressure-sensitive adhesive affixed on edge portions of the other face of the backing sheet for adhering the pad to a substrate, said pressure-sensitive adhesive being provided with a releasable cover sheet, and said adhesive strips are provided in the form of tape bearing pressure-sensitive adhesive on both sides thereof, one side of such tape being adhered to the exposed surface of the backing sheet, the adhesive strength on said one side of the tape being greater than the adhesive strength on the outer side of the tape.

2. A pad according to claim 1, wherein said pressure-sensitive adhesive is an acrylic adhesive.

3. A pad according to claim 1, which is rectangular and said adhesive strips are disposed adjacent to two parallel long edges of the backing sheet.

4. A pad according to claim 3, wherein the adhesive strength on said one side of the tape is from about 30 to about 112 ounces per inch of tape width and the adhesive strength on the other side of the tape is from about 20 to about 49 ounces per inch of tape width and the ratio of the adhesive strength on said one side of the tape to the adhesive strength on the other side of the tape is from about 1.5:1 to about 2.5:1.

5. A pad according to claim 3, wherein the adhesive strength on said one side of the tape is from about 60 to about 68 ounces per inch of tape width and the adhesive strength on the other side of the tape is from about 32 to about 37 ounces per inch of tape width and the ratio of the adhesive strength on said one side of the tape to the adhesive strength on the other side of the tape is from about 1.9:1 to about 2.1:1.

6. A pad according to claim 1, comprising an absorbent core layer of cellulosic material.

7. A pad according to claim 1, comprising an absorbent core layer of hydrophilic foamed synthetic resin.

8. A pad according to claim 1, wherein the fluid-impervious backing sheet comprises a film of plastics material.

9. A pad according to claim 1, wherein the facing layer is a nonwoven fabric.

10. An underpad which comprises a rectangular fluid-impervious backing sheet about 76 cm long and about 55 cm wide of opaque coloured polyethylene about 25 microns thickness; a fluid-absorbent layer, substantially coextensive with and adhesively bonded to said backing sheet, of four-ply unbleached crepe tissue wherein each ply weighs about 25.5 grams per square meter, the two long edges of the backing sheet being folded over the absorbent layer; a strip of double-sided pressure-sensitive adhesive tape applied to the major face of the backing sheet opposite the absorbent layer, near and along the length of each long edge of the pad, said strip being covered by an outer silicone impregnated release paper; and a facing layer of water repellent nonwoven fabric of about 70 grams per square meter covering the face of the absorbent layer opposite the backing sheet.

* * * * *